United States Patent
Zhang et al.

(10) Patent No.: US 12,157,916 B2
(45) Date of Patent: Dec. 3, 2024

(54) MITOCHONDRIAL DNA QUALITY CONTROL

(71) Applicant: Regeneron Pharmaceuticals, Inc., Tarrytown, NY (US)

(72) Inventors: Ruoyu Zhang, Tarrytown, NY (US); Wei Keat Lim, Tarrytown, NY (US); Gurinder Atwal, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 509 days.

(21) Appl. No.: 17/395,566

(22) Filed: Aug. 6, 2021

(65) Prior Publication Data
US 2022/0042091 A1 Feb. 10, 2022

Related U.S. Application Data

(60) Provisional application No. 63/062,566, filed on Aug. 7, 2020.

(51) Int. Cl.
| | |
|---|---|
| *C12Q 1/6869* | (2018.01) |
| *C12Q 1/6806* | (2018.01) |
| *G16B 20/20* | (2019.01) |
| *G16B 30/10* | (2019.01) |
| *G16B 30/20* | (2019.01) |
| *G16B 40/00* | (2019.01) |
| *G16B 40/20* | (2019.01) |

(52) U.S. Cl.
CPC ......... *C12Q 1/6869* (2013.01); *C12Q 1/6806* (2013.01); *G16B 20/20* (2019.02); *G16B 30/10* (2019.02); *G16B 30/20* (2019.02); *G16B 40/00* (2019.02); *G16B 40/20* (2019.02); *C12Q 2600/166* (2013.01)

(58) Field of Classification Search
None
See application file for complete search history.

(56) References Cited

PUBLICATIONS

Ye et al. "High-throughput sequencing in mitochondrial DNA research." Mitochondrion, vol. 17, pp. 157-163. (Year: 2014).*
Qian et al. "Approach, Application, and Bioethics of mtDNA Sequencing in Cancer." Mitochondrial DNA and Diseases, Advances in Experimental Medicine and Biology, 1038, H. Sun, X. Wang (eds.), Chapter 3, pp. 23-38. (Year: 2017).*
D'Aquila et al. "Mitochondrial genome and epigenome: two sides of the same coin." Frontiers in Bioscience, Landmark, vol. 22, pp. 888-908. (Year: 2017).*
Kaufman et al. "Electronic patient identification for sample labeling reduces wrong blood in tube errors." Transfusion, vol. 59, pp. 972-980. (Year: 2019).*
Weissensteiner et al. "Haplocheck: Phylogeny-based Contamination Detection in Mitochondrial and Whole-Genome Sequencing Studies." bioRxiv; posted Jul. 17; doi: https://doi.org/10.1101/2020.05.06.080952; pp. 1-25. (Year: 2020).*
Bandelt et al., "Contamination and sample mix-up can best explain some patterns of mtDNA instabilities in buccal cells and oral squamous cell carcinoma", BMC Cancer, 2009, 9(113), pp. 1-8.
Costello et al., "Characterization and remediation of sample index swaps by non-redundant dual indexing on massively parallel sequencing platforms", BMC Genomics, 2018, 19(332) pp. 1-10.
Diroma et al., "Extraction and annotation of human mitochondrial genomes from 1000 Genomes Whole Exome Sequencing data", BMC Genomics, 2014, 15, pp. 1-15.
Gunnarsdottir et al., "Larger mitochondrial DNA than Y-chromosome differences between matrilocal and patrilocal groups from Sumatra", Nature Commun, 2011, 2(228), pp. 1-7.
Huang et al., "Early Transcriptomic Changes in the Ileal Pouch Provide Insight into the Molecular Pathogenesis of Pouchitis and Ulcerative Colitis", Inflamm Bowel Dis, 2017, 23(3), pp. 366-378.
Lerner et al., "Incidence of misattributed specimen provenance among surgical breast biopsies", Cancer Res, 2015, 75(9 Suppl): Abstract nr P5-02-08.
Palanichamy et al., "Potetial pitfalls in MitoChip detected tumor-specific somatic mutations: a call for caution when interpreting patient data", BMC Cancer, 2010, 10(597), pp. 1-5.
Pfeifer et al., "Rate of Occult Specimen Provenance Complications in Routine Clinical Practice", Amer J Clin Pathol, 2013, 139, pp. 93-100.
Sehn et al., "Occult Specimen Contamination in Routine Clinical Next-Generation Sequencing Testing", Amer J Clin Pathol, 2015, 144(4), pp. 667-674.
Shen et al., "Evaluating mitochondrial DNA in patients with breast cancer and benign breast disease", J Cancer Res Clin Oncol, 2011, 137, pp. 669-675.
Slatkin et al., "Pairwise comparisons of mitochondrial DNA sequences in stable and exponentially growing populations", Genetics, 1991, 129(2), pp. 555-562.
Wu et al., "Circular RNA circCORO1C promotes laryngeal squamous cell carcinoma progression by modulating the let-7c-5p/PBX3 axis", Molec Cancer, 2020, 19(99), pp. 1-18.
Ye et al., "Extensive pathogenicity of mitochondrial heteroplasmy in healthy human individuals", PNAS, 2014, 111(29), pp. 10654-10659.
Zaragoza et al., "Mitochondrial DNA Variant Discovery and Evaluation in Human Cardiomyopathies through Next-Generation Sequencing", PLoS One, 2010, 5(8), pp. e12295.
Zhang et al., "Independent impacts of aging on mitochondrial DNA quantity and quality in humans", BMC Genomics, 2017, 18(890) pp. 1-14.

* cited by examiner

*Primary Examiner* — John S Brusca
*Assistant Examiner* — Steven W. Bailey
(74) *Attorney, Agent, or Firm* — Armstrong Teasdale LLP

(57) ABSTRACT

The present disclosure provides methods of identifying unreliable biological samples that may be mislabeled or contaminated, by determining the heteroplasmy and homoplasmy of mitochondrial DNA present in the biological samples.

19 Claims, 19 Drawing Sheets

| Digital contamination level | Heteroplasmy detected | Primary haplogroup | Secondary haplogroup | Heteroplasmy frequency mean | Heteroplasmy frequency median | Heteroplasmy frequency sd |
|---|---|---|---|---|---|---|
| 0.1% | 1 | U5a2a1a | U5a2a1a | 1.4% | 1.4% | NA |
| 0.5% | 11 | U5a2a1a | U5a2a1a | 1.6% | 1.5% | 0.4% |
| 1% | 29 | U5a2a1a | D4b1a1 | 1.9% | 1.7% | 0.8% |
| 2% | 45 | U5a2a1a | D4b1a1 | 3.1% | 2.9% | 1.5% |
| 5% | 46 | U5a2a1a | D4b1a1 | 6.9% | 6.6% | 3.0% |
| 10% | 46 | U5a2a1a | D4b1a1 | 13.1% | 12.8% | 5.1% |
| 20% | 46 | U5a2a1a | D4b1a1 | 24.8% | 25.0% | 8.1% |
| 30% | 46 | U5a2a1a | D4b1a1 | 35.2% | 36.3% | 10.2% |
| 40% | 45 | U5a2a1a | D4b1a1 | 42.1% | 44.1% | 7.3% |

FIG. 3

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493849 | IL1 | L3e2a1b1 | L3e2a1b1 | 1 | Normal | Ile | NA | pair |
| SRR3493850 | IL2 | L2a1l2a | L2a1l2a | 0 | Normal | Ile | NA | pair |
| SRR3493799 | P427 | H4 | H4 | 1 | Ulcerative colitis | Prepouch ileum | 4mo | pair |
| SRR3493809 | P427 | H4 | H4 | 1 | Ulcerative colitis | Prepouch ileum | 8mo | pair |
| SRR3493818 | P427 | H4 | H4 | 2 | Ulcerative colitis | Prepouch ileum | 12mo | pair |
| SRR3493828 | P427 | H4 | H4 | 1 | Ulcerative colitis | Ileal pouch | 4mo | pair |
| SRR3493838 | P427 | H4 | H4 | 1 | Ulcerative colitis | Ileal pouch | 12mo | pair |
| SRR3493790 | P501 | T2f1a1 | T2f1a1 | 1 | Ulcerative colitis | Ileal pouch | 4mo | pair |
| SRR3493791 | P501 | T2f1a1 | T2f1a1 | 0 | Ulcerative colitis | Ileal pouch | 8mo | pair |
| SRR3493792 | P501 | T2f1a1 | T2f1a1 | 1 | Ulcerative colitis | Ileal pouch | 12mo | pair |
| SRR3493839 | P501 | T2f1a1 | T2f1a1 | 1 | Ulcerative colitis | Prepouch ileum | 4mo | pair |
| SRR3493840 | P501 | T2f1a1 | T2f1a1 | 0 | Ulcerative colitis | Prepouch ileum | 8mo | pair |

FIG. 4A

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493841 | P501 | T2f1a1 | T2f1a1 | 0 | Ulcerative colitis | Prepouch ileum | 12mo | pair |
| SRR3493846 | P502 | J1c3a1 | J1c3a1 | 1 | Ulcerative colitis | Ileal pouch | 12mo | pair |
| SRR3493793 | P503 | H49a2 | H49a2 | 1 | Ulcerative colitis | Prepouch ileum | 4mo | pair |
| SRR3493794 | P503 | H49a2 | H49a | 1 | Ulcerative colitis | Prepouch ileum | 8mo | pair |
| SRR3493795 | P503 | H49a2 | H49a2 | 0 | Ulcerative colitis | Prepouch ileum | 12mo | pair |
| SRR3493796 | P503 | H49a2 | H49a2 | 0 | Ulcerative colitis | Ileal pouch | 8mo | pair |
| SRR3493797 | P503 | H49a2 | H49a2 | 0 | Ulcerative colitis | Ileal pouch | 12mo | pair |
| SRR3493798 | P505 | U1a1a1a | U1a1a1a | 1 | Ulcerative colitis | Prepouch ileum | 8mo | pair |
| SRR3493800 | P505 | U1a1a1a | U1a1a1a | 1 | Ulcerative colitis | Prepouch ileum | 12mo | pair |
| SRR3493801 | P505 | U1a1a1a | U1a1a1a | 1 | Ulcerative colitis | Ileal pouch | 4mo | pair |
| SRR3493802 | P505 | U1a1a1a | U1a1a | 0 | Ulcerative colitis | Ileal pouch | 8mo | pair |
| SRR3493803 | P505 | U1a1a1a | U1a1a1a | 1 | Ulcerative colitis | Ileal pouch | 12mo | pair |

FIG. 4B

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493804 | P506 | L1b2a | L1b2a | 0 | Ulcerative colitis | Prepouch ileum | 4mo | pair |
| SRR3493805 | P506 | L1b2a | L1b2a | 0 | Ulcerative colitis | Prepouch ileum | 12mo | pair |
| SRR3493806 | P506 | L1b2a | L1b2 | 1 | Ulcerative colitis | Ileal pouch | 4mo | pair |
| SRR3493807 | P506 | L1b2a | L1b2a | 1 | Ulcerative colitis | Ileal pouch | 8mo | pair |
| SRR3493808 | P506 | L1b2a | L1b2 | 2 | Ulcerative colitis | Ileal pouch | 12mo | pair |
| SRR3493810 | P507 | H1+16311 | H1e8 | 1 | Ulcerative colitis | Prepouch ileum | 4mo | pair |
| SRR3493811 | P507 | H1+16311 | H1+16311 | 1 | Ulcerative colitis | Ileal pouch | 4mo | pair |
| SRR3493812 | P508 | H1a | H1a | 2 | Ulcerative colitis | Prepouch ileum | 4mo | pair |
| SRR3493813 | P508 | H1a | H1a | 2 | Ulcerative colitis | Prepouch ileum | 8mo | pair |
| SRR3493814 | P508 | H1a | H1a | 0 | Ulcerative colitis | Ileal pouch | 4mo | pair |
| SRR3493815 | P508 | H1a | H1a | 1 | Ulcerative colitis | Ileal pouch | 8mo | pair |
| SRR3493816 | P509 | N1a1a1a1 | N1a1a1a1 | 1 | Ulcerative colitis | Prepouch ileum | 4mo | pair |

FIG. 4C

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493817 | P509 | N1a1a1a1 | N1a1a1a1 | 0 | Ulcerative colitis | Ileal pouch | 4mo | pair |
| SRR3493819 | P510 | K1a1b1a | K1a1b1a | 0 | Ulcerative colitis | Prepouch ileum | 4mo | pair |
| SRR3493820 | P510 | K1a1b1a | K1a1b1a | 2 | Ulcerative colitis | Ileal pouch | 4mo | pair |
| SRR3493821 | P511 | H1ar1 | H1ar1 | 3 | Ulcerative colitis | Prepouch ileum | 4mo | pair |
| SRR3493822 | P511 | H1ar1 | H1ar1 | 2 | Ulcerative colitis | Prepouch ileum | 8mo | pair |
| SRR3493823 | P511 | H1ar1 | H1ar1 | 3 | Ulcerative colitis | Ileal pouch | 4mo | pair |
| SRR3493824 | P511 | H1ar1 | H1ar1 | 3 | Ulcerative colitis | Ileal pouch | 8mo | pair |
| SRR3493825 | P512 | I1a1a | I1a1a | 1 | Ulcerative colitis | Ileal pouch | 4mo | pair |
| SRR3493826 | P513 | T1a1 | T1a1 | 0 | Ulcerative colitis | Prepouch ileum | 4mo | pair |
| SRR3493827 | P513 | T1a1 | T1a1 | 1 | Ulcerative colitis | Ileal pouch | 4mo | pair |
| SRR3493829 | P600 | T2b36 | T2b36 | 1 | Ulcerative colitis | Prepouch ileum | 4mo | pair |
| SRR3493830 | P600 | T2b36 | T2b36 | 0 | Ulcerative colitis | Prepouch ileum | 8mo | pair |

FIG. 4D

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493831 | P600 | T2b36 | T2b36 | 0 | Ulcerative colitis | Ileal pouch | 4mo | pair |
| SRR3493832 | P600 | T2b36 | T2b36 | 0 | Ulcerative colitis | Ileal pouch | 8mo | pair |
| SRR3493844 | P601 | T2b21 | T2b21b | 0 | FAP | Prepouch ileum | >12mo | pair |
| SRR3493845 | P601 | T2b21 | T2b21 | 1 | FAP | Ileal pouch | >12mo | pair |
| SRR3493847 | P602 | J1c1b1 | J1c1b1 | 1 | Ulcerative colitis | Ileal pouch | 12mo | pair |
| SRR3493848 | P602 | J1c1b1a | J1c1b1a | 29 | Ulcerative colitis | Prepouch ileum | 12mo | pair |
| SRR3493833 | P604 | U5b2a1a1 | J1c8a | 1 | Ulcerative colitis | Prepouch ileum | 8mo | pair |
| SRR3493834 | P604 | U5b2a1a1 | U5b2a1a1 | 1 | Ulcerative colitis | Ileal pouch | 8mo | pair |
| SRR3493835 | P604 | U5b2a1a1 | U5b2a1a1 | 1 | Ulcerative colitis | Prepouch ileum | 12mo | pair |
| SRR3493836 | P607 | H1c1 | H1c1 | 0 | Ulcerative colitis | Ileal pouch | 4mo | pair |
| SRR3493837 | P607 | H1c1 | H1e8 | 1 | Ulcerative colitis | Ileal pouch | 4mo | pair |
| SRR3493842 | P701 | H6a1b4 | H6a1b4 | 0 | FAP | Prepouch ileum | >12mo | pair |

FIG. 4E

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493843 | P701 | H6a1b4 | H6a1b4 | 0 | FAP | Ileal pouch | >12mo | pair |
| SRR3493774 | P500 | J1c8a | J1c8a | 5 | Ulcerative colitis | Ileal pouch | 4mo | single |
| SRR3493775 | P500 | J1c8a | J1c8a | 3 | Ulcerative colitis | Prepouch ileum | 4mo | single |
| SRR3493776 | P500 | J1c8a | J1c8a | 5 | Ulcerative colitis | Ileal pouch | 8mo | single |
| SRR3493777 | P500 | J1c8a | J1c8a | 4 | Ulcerative colitis | Prepouch ileum | 8mo | single |
| SRR3493778 | P500 | J1c8a | J1c8 | 3 | Ulcerative colitis | Ileal pouch | 12mo | single |
| SRR3493779 | P500 | J1c8a | J1c8a | 4 | Ulcerative colitis | Prepouch ileum | 12mo | single |
| SRR3493780 | P502 | J1c3a1 | JT | 3 | Ulcerative colitis | Ileal pouch | 4mo | single |
| SRR3493781 | P502 | J1c3a1 | J1c3a1 | 4 | Ulcerative colitis | Prepouch ileum | 4mo | single |
| SRR3493782 | P502 | J1c3a1 | J1c3a1 | 3 | Ulcerative colitis | Ileal pouch | 8mo | single |
| SRR3493783 | P502 | J1c3a1 | J1c3a1 | 3 | Ulcerative colitis | Prepouch ileum | 8mo | single |
| SRR3493784 | P502 | J1c3a1 | J1c3a1 | 6 | Ulcerative colitis | Ileal pouch | 12mo | single |

FIG. 4F

| Sample ID | Patient ID | Primary haplogroup | Secondary haplogroup | Heteroplasmy number | Diagnosis | Tissue | Biopsy time | single/pair end |
|---|---|---|---|---|---|---|---|---|
| SRR3493785 | P502 | J1c3a1 | J1c3a1 | 3 | Ulcerative colitis | Prepouch ileum | 12mo | single |
| SRR3493786 | P602 | J1c1b1 | J1c1b1 | 2 | Ulcerative colitis | Ileal pouch | >12mo | single |
| SRR3493787 | P602 | J1c1b1 | J1c1b1 | 3 | Ulcerative colitis | Prepouch ileum | >12mo | single |
| SRR3493788 | P603 | H1j | H1j | 3 | Ulcerative colitis | Ileal pouch | >12mo | single |
| SRR3493789 | P603 | H1j | H1j | 1 | Ulcerative colitis | Prepouch ileum | >12mo | single |

FIG. 4G

| Sample ID | Subject ID | Tissue | Primary haplogroup | Secondary haplogroup | Heteroplasmy number |
|---|---|---|---|---|---|
| SRR8631600 | 1 | LSCC tissue | D5a2a2 | D5a2a2 | 0 |
| SRR8631657 | 1 | adjacent normal mucosa tissue | D5a2a2 | D5a2a2 | 0 |
| SRR8631601 | 2 | LSCC tissue | B5a | B5a | 3 |
| SRR8631658 | 2 | adjacent normal mucosa tissue | B5a | B5a | 0 |
| SRR8631602 | 3 | LSCC tissue | M8a3 | M8a3 | 2 |
| SRR8631659 | 3 | adjacent normal mucosa tissue | M8a3 | M8a3 | 0 |
| SRR8631603 | 4 | LSCC tissue | A13 | A13 | 0 |
| SRR8631660 | 4 | adjacent normal mucosa tissue | A13 | A13 | 0 |
| SRR8631604 | 5 | LSCC tissue | D4b2b | D4b2b | 0 |
| SRR8631661 | 5 | adjacent normal mucosa tissue | D4b2b | D4b2b | 0 |
| SRR8631605 | 6 | LSCC tissue | F1a1a | F1a1a | 1 |
| SRR8631662 | 6 | adjacent normal mucosa tissue | F1a1a | F1a1a | 0 |
| SRR8631606 | 7 | LSCC tissue | D2b1a | D2b1a | 0 |
| SRR8631663 | 7 | adjacent normal mucosa tissue | D2b1a | D2b1a | 0 |

FIG. 5A

| Sample ID | Subject ID | Tissue | Primary haplogroup | Secondary haplogroup | Heteroplasmy number |
| --- | --- | --- | --- | --- | --- |
| SRR8631664 | 8 | adjacent normal mucosa tissue | D4 | D4 | 0 |
| SRR8631607 | 8 | LSCC tissue | D4 | D4 | 0 |
| SRR8631608 | 9 | LSCC tissue | D4 | D4 | 1 |
| SRR8631665 | 9 | adjacent normal mucosa tissue | D4 | D4 | 1 |
| SRR8631609 | 10 | LSCC tissue | G1a1a | G1a1a | 0 |
| SRR8631666 | 10 | adjacent normal mucosa tissue | G1a1a | G1a1a | 0 |
| SRR8631667 | 11 | adjacent normal mucosa tissue | Z3d | Z3d | 1 |
| SRR8631610 | 11 | LSCC tissue | Z3d | Z3d | 0 |
| SRR8631668 | 12 | adjacent normal mucosa tissue | D4b2b6 | D4b2b6 | 0 |
| SRR8631611 | 12 | LSCC tissue | D4b2b6 | D4b2b6 | 0 |
| SRR8631612 | 13 | LSCC tissue | D4h1c | D4h1c | 3 |
| SRR8631669 | 13 | adjacent normal mucosa tissue | D4h1c | D4h1c | 2 |
| SRR8631613 | 14 | LSCC tissue | N9a10 | N9a10 | 1 |
| SRR8631670 | 14 | adjacent normal mucosa tissue | N9a10 | N9a10 | 0 |

FIG. 5B

| Sample ID | Subject ID | Tissue | Primary haplogroup | Secondary haplogroup | Heteroplasmy number |
|---|---|---|---|---|---|
| SRR8631614 | 15 | LSCC tissue | D5b1b | D5b1b | 0 |
| SRR8631671 | 15 | adjacent normal mucosa tissue | D5b1b | D5b1b | 0 |
| SRR8631615 | 16 | LSCC tissue | Z3d | Z3d | 1 |
| SRR8631672 | 16 | adjacent normal mucosa tissue | Z3d | Z3d | 0 |
| SRR8631673 | 17 | adjacent normal mucosa tissue | N9a8 | N9a8 | 2 |
| SRR8631616 | 17 | LSCC tissue | N9a8 | N9a8 | 0 |
| SRR8631617 | 18 | LSCC tissue | B4f | B4f | 0 |
| SRR8631674 | 18 | adjacent normal mucosa tissue | B4f | B4f | 0 |
| SRR8631618 | 19 | LSCC tissue | M9a1a1c1b | M9a1a1c1b | 0 |
| SRR8631675 | 19 | adjacent normal mucosa tissue | M9a1a1c1b | M9a1a1c1b | 0 |
| SRR8631619 | 20 | LSCC tissue | N9a1 | N9a1 | 0 |
| SRR8631676 | 20 | adjacent normal mucosa tissue | N9a1 | N9a1 | 0 |
| SRR8631677 | 22 | adjacent normal mucosa tissue | Z3a | Z3a | 0 |
| SRR8631620 | 22 | LSCC tissue | Z3a | Z3a | 0 |

FIG. 5C

| Sample ID | Subject ID | Tissue | Primary haplogroup | Secondary haplogroup | Heteroplasmy number |
|---|---|---|---|---|---|
| SRR8631621 | 23 | LSCC tissue | C5d | C5d | 1 |
| SRR8631678 | 23 | adjacent normal mucosa tissue | C5d | C5d | 0 |
| SRR8631622 | 24 | LSCC tissue | M7c1a2a | M7c1a2a | 3 |
| SRR8631679 | 24 | adjacent normal mucosa tissue | M7c1a2a | M7c1a2a | 1 |
| SRR8631623 | 25 | LSCC tissue | M9a1a1c1a | M9a1a1c1a | 1 |
| SRR8631680 | 25 | adjacent normal mucosa tissue | M9a1a1c1a | M9a1a1c1a | 0 |
| SRR8631681 | 26 | adjacent normal mucosa tissue | D4e5a | D4e5a | 1 |
| SRR8631624 | 26 | LSCC tissue | D4e5a | D4e5a | 0 |
| SRR8631625 | 27 | LSCC tissue | B4d1 | B4d1 | 3 |
| SRR8631682 | 27 | adjacent normal mucosa tissue | B4d1 | B4d1 | 4 |
| SRR8631626 | 28 | LSCC tissue | B5b1a1 | B5b1a1 | 0 |
| SRR8631683 | 28 | adjacent normal mucosa tissue | B5b1a1 | B5b1a1 | 0 |
| SRR8631627 | 29 | LSCC tissue | D4h1b | D4h1b | 2 |
| SRR8631684 | 29 | adjacent normal mucosa tissue | D4h1b | D4h1b | 0 |

FIG. 5D

| Sample ID | Subject ID | Tissue | Primary haplogroup | Secondary haplogroup | Heteroplasmy number |
|---|---|---|---|---|---|
| SRR8631628 | 30 | LSCC tissue | D4e5b | D4e5b | 1 |
| SRR8631685 | 30 | adjacent normal mucosa tissue | D4e5b | D4e5b | 1 |
| SRR8631629 | 31 | LSCC tissue | B4d1a | B4d1a | 1 |
| SRR8631686 | 31 | adjacent normal mucosa tissue | B4d1a | B4d1a | 0 |
| SRR8631630 | 34 | LSCC tissue | A6 | A6 | 0 |
| SRR8631687 | 34 | adjacent normal mucosa tissue | A6 | A6 | 0 |
| SRR8631631 | 35 | LSCC tissue | F3a | F3a | 2 |
| SRR8631688 | 35 | adjacent normal mucosa tissue | F3a | F3a | 1 |
| SRR8631632 | 36 | LSCC tissue | N9a | N9a | 1 |
| SRR8631689 | 36 | adjacent normal mucosa tissue | N9a | N9a | 0 |
| SRR8631633 | 37 | LSCC tissue | D5b1 | D5b1 | 1 |
| SRR8631690 | 37 | adjacent normal mucosa tissue | D5b1 | D5b1 | 0 |
| SRR8631691 | 46 | adjacent normal mucosa tissue | G2a | G2a | 0 |
| SRR8631634 | 46 | LSCC tissue | G2a'c | G2a'c | 0 |

FIG. 5E

| Sample ID | Subject ID | Tissue | Primary haplogroup | Secondary haplogroup | Heteroplasmy number |
|---|---|---|---|---|---|
| SRR8631635 | 50 | LSCC tissue | A13 | A13 | 0 |
| SRR8631692 | 50 | adjacent normal mucosa tissue | A13 | A13 | 0 |
| SRR8631636 | 51 | LSCC tissue | D5b1b | D5b1b | 1 |
| SRR8631693 | 51 | adjacent normal mucosa tissue | D5b1b | D5b1b | 0 |
| SRR8631694 | 52 | adjacent normal mucosa tissue | F1g | F1g | 2 |
| SRR8631637 | 52 | LSCC tissue | F1 | F1 | 0 |
| SRR8631695 | 53 | adjacent normal mucosa tissue | F1g | F1g | 1 |
| SRR8631638 | 53 | LSCC tissue | F1g | F1g | 0 |
| SRR8631696 | 54 | adjacent normal mucosa tissue | M7c1a | M7c1a | 0 |
| SRR8631639 | 54 | LSCC tissue | M7c1a | M7c1a | 0 |
| SRR8631640 | 55 | LSCC tissue | B4h | B4h | 2 |
| SRR8631697 | 55 | adjacent normal mucosa tissue | B4h | B4h | 1 |
| SRR8631641 | 56 | LSCC tissue | F1a1 | F1a1 | 1 |
| SRR8631698 | 56 | adjacent normal mucosa tissue | F1a1 | F1a1 | 0 |

FIG. 5F

| Sample ID | Subject ID | Tissue | Primary haplogroup | Secondary haplogroup | Heteroplasmy number |
|---|---|---|---|---|---|
| SRR8631642 | 57 | LSCC tissue | N9a2 | N9a2 | 2 |
| SRR8631699 | 57 | adjacent normal mucosa tissue | N9a2 | N9a2 | 4 |
| SRR8631643 | 58 | LSCC tissue | G2a1d | G2a1d | 1 |
| SRR8631700 | 58 | adjacent normal mucosa tissue | G2a1d | G2a1d | 0 |
| SRR8631644 | 59 | LSCC tissue | Z3d | Z3d | 0 |
| SRR8631701 | 59 | adjacent normal mucosa tissue | Z3d | Z3d | 0 |
| SRR8631645 | 60 | LSCC tissue | A+152+16362+200 | A+152+16362+200 | 1 |
| SRR8631702 | 60 | adjacent normal mucosa tissue | A+152+16362+200 | A+152+16362+200 | 1 |
| SRR8631646 | 61 | LSCC tissue | B4d3a | B4d3a | 1 |
| SRR8631703 | 61 | adjacent normal mucosa tissue | B4d3a | B4d3a | 1 |
| SRR8631647 | 62 | LSCC tissue | A+152+16362 | A+152+16362 | 3 |
| SRR8631704 | 62 | adjacent normal mucosa tissue | A+152+16362 | A+152+16362 | 0 |
| SRR8631648 | 63 | LSCC tissue | I2 | I2 | 1 |
| SRR8631705 | 63 | adjacent normal mucosa tissue | I2 | I2 | 0 |

FIG. 5G

| Sample ID | Subject ID | Tissue | Primary haplogroup | Secondary haplogroup | Heteroplasmy number |
|---|---|---|---|---|---|
| SRR8631649 | 64 | LSCC tissue | M12a1a | M12a1a | 1 |
| SRR8631706 | 64 | adjacent normal mucosa tissue | M12a1a | M12a1a | 0 |
| SRR8631650 | 65 | LSCC tissue | N9a3 | N9a3 | 1 |
| SRR8631707 | 65 | adjacent normal mucosa tissue | N9a3 | N9a3 | 0 |
| SRR8631651 | 66 | LSCC tissue | F1a1c | F1a1c | 1 |
| SRR8631708 | 66 | adjacent normal mucosa tissue | F1a1c2 | F1a1c2 | 1 |
| SRR8631709 | 73 | adjacent normal mucosa tissue | D5a2a1 | D5a2a1 | 0 |
| SRR8631652 | 73 | LSCC tissue | D5a2a1+@16172 | D5a2a1+@16172 | 0 |
| SRR8631653 | 74 | LSCC tissue | A15a | A15a | 2 |
| SRR8631710 | 74 | adjacent normal mucosa tissue | A15a | A15a | 0 |
| SRR8631654 | 75 | LSCC tissue | B4a1 | B4a1 | 2 |
| SRR8631711 | 75 | adjacent normal mucosa tissue | B4a1 | B4a1 | 0 |
| SRR8631655 | 76 | LSCC tissue | F1a1c | F1a1c | 2 |
| SRR8631712 | 76 | adjacent normal mucosa tissue | F1a1c | F1a1c | 0 |
| SRR8631656 | 77 | LSCC tissue | M7a1a1a | M7a1a1a | 1 |
| SRR8631713 | 77 | adjacent normal mucosa tissue | M7a1a1a | M7a1a1a | 0 |

FIG. 5H

MITOCHONDRIAL DNA QUALITY CONTROL

FIELD

The present disclosure is directed, in part, to methods of identifying unreliable biological samples that may be mislabeled or contaminated.

BACKGROUND

For over 10 years, next-generation sequencing (NGS) has become an important component in biological and biomedical researches because it makes sequencing of large batches of DNA or RNA samples feasible. NGS has broad applications, such as whole genome and whole exome sequencing for large cohort genetic investigation, bulk RNA-seq for disease gene expression signatures identification in clinical evaluation, tissue biopsy sequencing in tumor study/diagnostic and recently emerged single-cell sequencing research, providing answers and solutions to many different problems and questions. However, in the studies involving large-scale samples, sample identity complication is a common and almost inevitable problem. The estimate sample identity error rate can range from 0.2% to 6% in practice (Pfeifer et al., Amer. J. Clin. Pathol., 2013, 139, 93-100; Costello et al., BMC Genomics, 2018, 19, 332; Lerner et al., Cancer Res., 2015, 75, Abstract P5-02-08; and Sehn et al., Amer. J. Clin. Pathol., 2015. 144, 667-674). The errors can happen at different degrees: 1) a complete swapping between samples, and/or 2) contamination of one sample with one or more other samples. Various steps during the sample processing can introduce the errors, such as sample mislabeling during sample collection, material spillage during pipetting, index swapping in pooled libraries when performing sequencing and many other unexpected situations. Sample swapping/contamination will subsequently reduce the quality and accuracy of the downstream analysis. For example, sample swapping in a whole transcriptome analysis may lead to false discovery or lose power to detect differentially expressed genes. In cancer studies, somatic mutation identification is routinely used, given that many of those mutations were present at very low frequency (<5%), thus even low levels (1% to 5%) of contamination may result in false positive mutation callings. For those reasons, accurate detection of sample swapping and contamination is an important quality control step in large scale NGS studies.

Mitochondria are essential organelles in most eukaryotic cells. Human mitochondrial DNA (mtDNA) are 16.5 kb circular DNA molecules located in mitochondria, and encode gene products that are essential for mitochondrial functions. There are hundreds to thousands of mtDNA copies within a single cell. mtDNA is maternally inherited with negligible recombination. Because mtDNA is uniparentally inherited and undergoes negligible recombination at a population level, mutations acquired over time have subdivided the human population into several discrete mtDNA haplogroups. On average, two random individuals will have 30 to 40 nucleotide differences in their mitochondrial genome (Gunnarsdóttir et al., Nature Commun., 2011, 2, 228; Slatkin et al., Genetics, 1991, 129, 555-562; and Ye et al., Proc. Nat'l Acad. Sci. USA, 2014, 111, E4548-E4550). Because of its multi-copy nature, mtDNA mutations often only present in a small proportion of the cell's mtDNA, a state termed as heteroplasmy. The percentage of mtDNA carrying the mutation is referred as heteroplasmy frequency. In contrast, if a mutation is found in all mtDNA molecules, this mutation will be termed as homoplasmy. Previous studies demonstrated that in general healthy populations, most individuals will harbor less than 5 heteroplasmies (with frequency >1 to 2%) in their mitochondrial genome (Zhang et al., BMC Genomics, 2017, 18, 890; and Ye et al., Proc. Nat'l Acad. Sci. USA, 2014, 111, 10654-10659). For a batch of samples, samples collected from the same individual should all belong to the same haplogroup.

SUMMARY

The present disclosure provides methods of identifying an unreliable biological sample, the method comprising: a) performing a nucleic acid sequencing assay on each biological sample of a plurality of biological samples obtained from a single individual to obtain mitochondrial DNA (mtDNA) sequencing reads for each biological sample; b) identifying a heteroplasmy and a homoplasmy in the mtDNA sequencing reads from the previous step for each of the biological samples; and c) assigning a primary mtDNA haplogroup to each biological sample, wherein any biological sample having an assigned primary mtDNA haplogroup that is different than the primary mtDNA haplogroup assigned to a majority of the biological samples from the same individual is an unreliable biological sample that is a mislabeled biological sample.

The present disclosure also provides methods of identifying an unreliable biological sample, the method comprising: a) performing a nucleic acid sequencing assay on each biological sample of a plurality of biological samples obtained from a single individual to obtain mitochondrial DNA (mtDNA) sequencing reads for each biological sample; b) identifying a heteroplasmy and a homoplasmy in the mtDNA sequencing reads from the previous step for each of the biological samples; c) assigning a primary mtDNA haplogroup to each biological sample; and d) determining the total heteroplasmy number for each biological sample, wherein when a biological sample has a high heteroplasmy number, the biological sample is assigned a secondary mtDNA haplogroup based on the minor alleles in the heteroplasmy sites, wherein a biological sample having an assigned secondary mtDNA haplogroup that is different than the assigned primary mtDNA haplogroup is an unreliable sample that is contaminated.

The present disclosure also provides methods of identifying an unreliable biological sample, the method comprising: a) performing a nucleic acid sequencing assay on each biological sample of a plurality of biological samples obtained from a single individual to obtain mitochondrial DNA (mtDNA) raw sequencing reads for each biological sample; b) processing the mtDNA raw sequencing reads for quality control and adaptor sequence removal to produce quality controlled mtDNA sequencing reads; c) mapping the quality controlled mtDNA sequencing reads to a mitochondrial reference genome to produce candidate mtDNA sequencing reads; d) re-mapping the candidate mtDNA sequencing reads to a human reference genome and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5; e) performing post-mapping processing of the retained candidate mtDNA sequencing reads for sorting and duplicate removal; f) identifying heteroplasmy and homoplasmy in the retained candidate mtDNA sequencing reads for each of the biological samples; and g) assigning a primary mtDNA haplogroup to each biological sample, wherein any biological sample having an assigned primary mtDNA haplogroup that is different than the primary mtDNA haplogroup assigned to a majority of the biological samples from the same individual is an unreliable biological sample that is a mislabeled biological sample.

The present disclosure also provides methods of identifying an unreliable biological sample, the method comprising: a) performing a nucleic acid sequencing assay on each biological sample of a plurality of biological samples obtained from a single individual to obtain mitochondrial DNA (mtDNA) raw sequencing reads for each biological sample; b) processing the mtDNA raw sequencing reads for quality control and adaptor sequence removal to produce quality controlled mtDNA sequencing reads; c) mapping the quality controlled mtDNA sequencing reads to a mitochondrial reference genome to produce candidate mtDNA sequencing reads; d) re-mapping the candidate mtDNA sequencing reads to a human reference genome and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5; e) performing post-mapping processing of the retained candidate mtDNA sequencing reads for sorting and duplicate removal; f) identifying heteroplasmy and homoplasmy in the retained candidate mtDNA sequencing reads for each of the biological samples; g) assigning a primary mtDNA haplogroup to each biological sample; and h) determining the total heteroplasmy number for each biological sample, wherein when a biological sample has a high heteroplasmy number, the biological sample is assigned a secondary mtDNA haplogroup, wherein a biological sample having an assigned secondary mtDNA haplogroup that is different than the assigned primary mtDNA haplogroup is an unreliable sample that is contaminated.

BRIEF DESCRIPTION OF THE DRAWINGS

FIG. 3 shows results of contamination detection in virtual contamination samples.

FIG. 4A shows results from sample swapping and contamination detection in RNA-seq data 1.

FIG. 4B shows results from sample swapping and contamination detection in RNA-seq data 1.

FIG. 4C shows results from sample swapping and contamination detection in RNA-seq data 1.

FIG. 4D shows results from sample swapping and contamination detection in RNA-seq data 1.

FIG. 4E shows results from sample swapping and contamination detection in RNA-seq data 1.

FIG. 4F shows results from sample swapping and contamination detection in RNA-seq data 1.

FIG. 4G shows results from sample swapping and contamination detection in RNA-seq data 1.

FIG. 5A shows results from sample swapping and contamination detection in RNA-seq data 2.

FIG. 5B shows results from sample swapping and contamination detection in RNA-seq data 2.

FIG. 5C shows results from sample swapping and contamination detection in RNA-seq data 2.

FIG. 5D shows results from sample swapping and contamination detection in RNA-seq data 2.

FIG. 5E shows results from sample swapping and contamination detection in RNA-seq data 2.

FIG. 5F shows results from sample swapping and contamination detection in RNA-seq data 2.

FIG. 5G shows results from sample swapping and contamination detection in RNA-seq data 2.

FIG. 5H shows results from sample swapping and contamination detection in RNA-seq data 2.

DESCRIPTION OF EMBODIMENTS

Figure 1:
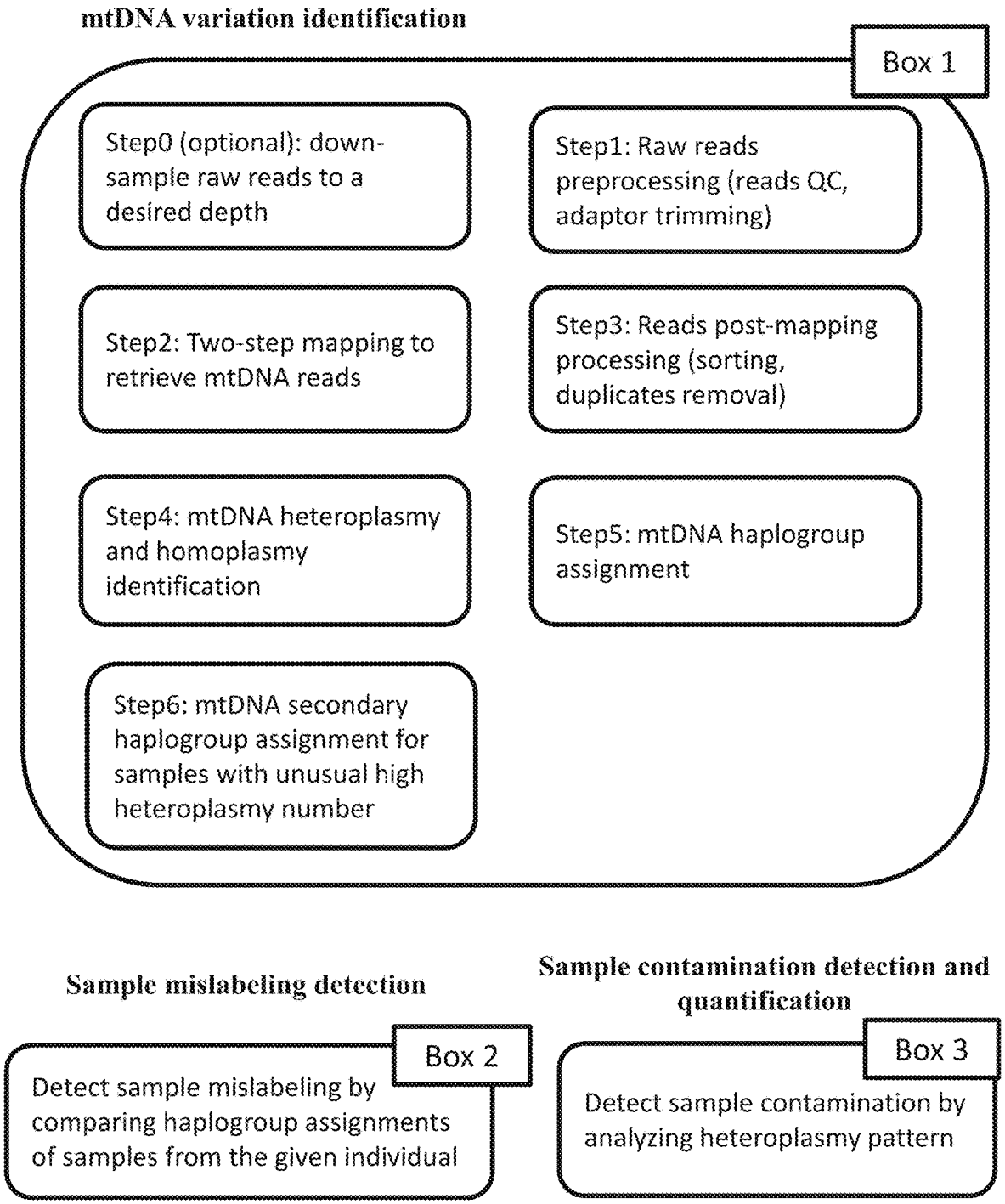
FIG. 1 shows a representative schematic showing suitable steps for carrying out the quality control analysis described herein. In Box 1, mtDNA homoplasmies and heteroplasmies are identified from fastq files. An optional down sampling step can be applied for sample with high mtDNA coverage. After reads QC, mtDNA reads are selected by a two-step mapping strategy. mtDNA variants ware identified from the mtDNA mapping results and primary and secondary mtDNA haplogroup are assigned to each sample based on the variants information. In Box 2, sample swapping/mislabeling can be detected by comparing haplogroup assignments of samples from the given individual. In Box 3, sample contamination can be detected by unusual high mtDNA heteroplamsy number and unmatched primary and secondary haplogroup groups.

Methods are presented herein for leveraging mtDNA sequences information to detect potential sample mislabeling and contaminations in NGS data. mtDNA polymorphisms and mutations can be used to infer the identity of a particular biological sample, and act as an indicator of sample mislabeling. In addition, when a biological sample is contaminated by DNA/RNA from another biological sample, unusual mtDNA mutation patterns will be revealed, which can help identify and further quantify the contaminant. Compared to nuclear DNA mutation-based approaches, the methods described herein allows for higher sensitivity even in low coverage sequencing data.

The methods described herein can take any NGS data containing sufficient mtDNA reads as input, identify mtDNA variants (heteroplamsy and homoplasmy) from the data, and use the variants information to assign haplogroups to each sample to detect potential sample swapping or mislabeling. By evaluating the samples' heteroplasmy information, the methods described herein can further detect cross-individual contamination.

The terminology used herein is for the purpose of describing particular embodiments only and is not intended to be limiting.

A human will have wild type (or reference) mtDNA molecules and may have mutant mtDNA molecules. If a human has no mutant mtDNA molecules, such a human is considered to be homoplasmic wild type (or homoplasmic reference). If a human has no wild type mtDNA molecules (i.e., only has mutant mtDNA), such a human is considered to be homoplasmic mutant. Homoplasmy is, thus, a measure of possessing all or no copies of mutant mtDNA.

If a human possesses a mixture of wild type and mutant mtDNA molecules, the human is considered to possess a heteroplasmy. The fraction of mutated copies is referred to herein as the "heteroplasmy frequency." For example, assuming a human has 8 copies of mtDNA molecules, and possesses a single copy of the eight mtDNA molecules that has a particular mutation in gene A, such a human is considered to have a heteroplasmy frequency of 12.5% (i.e., ⅛). Heteroplasmy can be determined for each mutation within the mtDNA genome for a particular individual. Thus, an individual having 2 mtDNA mutations (relative to wild type mtDNA) can have two heteroplasmies. Each heteroplasmy is associated with its own heteroplasmy frequency.

The present disclosure provides methods of identifying an unreliable biological sample. The methods comprise performing a nucleic acid sequencing assay on each biological sample of a plurality of biological samples obtained from a single individual to obtain mitochondrial DNA (mtDNA) sequencing reads for each biological sample. The methods also comprise identifying the presence of one or more heteroplasmies and homoplasmies in the mtDNA sequencing reads for each of the biological samples. The methods also comprise assigning a primary mtDNA haplogroup to each biological sample. A biological sample that has an assigned primary mtDNA haplogroup that is different than the primary mtDNA haplogroup assigned to a majority of the biological samples from the same individual is an unreliable biological sample. Such an unreliable biological sample may have been, for example, mislabeled or swapped with another biological sample.

The nucleic acid sequencing assay is any nucleic acid sequencing protocol. In some embodiments, the sequencing assay comprises next generation sequencing (NGS). In some embodiments, the NGS comprises whole genome sequencing. In some embodiments, the NGS comprises whole exome sequencing. In some embodiments, the NGS comprises RNA sequencing. In some embodiments, the NGS comprises bisulfite sequencing.

The nucleic acid sequencing assay is performed on each biological sample of a plurality of biological samples obtained from a single individual. In some embodiments, the plurality of biological samples can number from as low as 2 to thousands of samples. In some embodiments, the plurality of biological samples can number from as low as 2 to hundreds of samples. In some embodiments, the plurality of biological samples is obtained from one or more clinical studies. In some embodiments, the single individual's plurality of biological samples may be intermixed or batched with a plurality of biological samples from another individual. mtDNA sequencing reads for each biological sample are obtained.

The presence of one or more heteroplasmies and homoplasmies in the mtDNA sequencing reads for each of the biological samples is determined. Thus, for each mutation identified in the mtDNA sequencing reads, the heteroplasmy and homoplasmy analysis is performed. The sum of all the heteroplasmies is represented by the total heteroplasmy number for a particular biological sample. The mtDNA sequencing read information for each mtDNA mutational site is compiled to provide a summary of the sequencing information of mapped reads at each single site. In some embodiments, the compiling can be carried out using, for example, the samtools mpileup function (Li et al., Bioinformatics, 2009, 25, 2078-2079). The mtDNA sequencing read information for each mtDNA mutational site is filtered by sequence quality to, for example, remove sequencing bases with low sequencing quality to reduce sequencing errors. In some embodiments, a sequence quality score (Q) is determined, which is a property that is logarithmically related to the sequencing error probability ($Q=-10*\log_{10}(P)$, where P is the probability of a sequencing error). In some embodiments, the sequence quality Q is ≥20. When Q is 20, there is a 1% probability of a sequencing error.

In some embodiments, the heteroplasmy is identified by determining the sequencing coverage, the presence of a minor allele, and minor allele frequency. The sequencing coverage represents the number of reads that align to a known mtDNA reference base. In some embodiments, the sequencing coverage is ≥50. The sequencing coverage is generated by mpileup minus the bases with Q<20. In some embodiments, the minor allele frequency is ≥1% for DNA sequencing data and ≥5% for RNA sequencing data. In some embodiments, the minor allele is observed at least twice from each DNA strand, or the minor allele is observed at least three times for RNA. For example, the following mtDNA sequencing reads may be obtained (the first sequence is the reference sequence):

N1-N2-N3-N4-N5-N6-N7-N8-G9-N10-N11-N12-N13-N14-N15-N16-N17-N18-N19-N20 5'-N1-N2-N3-N4-N5-N6-N7-N8-A9-N10-N11-N12-N13-N14-N15-3'
3'-N2-N3-N4-N5-N6-N7-N8-A9-N10-N11-N12-N13-N14-N15-N16-5'
5'-N2-N3-N4-N5-N6-N7-N8-G9-N10-N11-N12-N13-N14-N15-N16-3'
5'-N3-N4-N5-N6-N7-N8-G9-N10-N11-N12-N13-N14-N15-N16-N17-3'
5'-N3-N4-N5-N6-N7-N8-G9-N10-N11-N12-N13-N14-N15-N16-N17-3'
3'-N3-N4-N5-N6-N7-N8-G9-N10-N11-N12-N13-N14-N15-N16-N17-5'
3'-N4-N5-N6-N7-N8-G9-N10-N11-N12-N13-N14-N15-N16-N17-N18-5'
5'-N7-N8-G9-N10-N11-N12-N13-N14-N15-N16-N17-N18-N19-N20-3'

The heteroplasmy frequency for this candidate mtDNA heteroplasmy site is 25% (⅖). In this particular analysis, the sequencing quality is >20 and the sequencing coverage is >50. The minor allele is observed in both strands of the DNA. Accordingly, this particular mutational site (i.e., a candidate mtDNA heteroplasmy site) is a mtDNA heteroplasmy.

In some embodiments, the homoplasmy is identified by determining the sequencing coverage and the presence of one or more alleles. A homoplasmy is present when: i) the sequencing coverage is >10; and ii) only one allele is observed at a particular nucleic acid mutation site and it is different than the corresponding reference allele, or multiple alleles are observed at a particular nucleic acid mutation site and the major allele is different than the corresponding reference allele, and the particular nucleic acid site is not a heteroplasmy and does not meet the heteroplasmy identification criteria.

In some embodiments, assigning the primary mtDNA haplogroup to each biological sample comprises constructing a mtDNA sequence for each biological sample. In some embodiments, the mtDNA sequence for each biological sample is constructed using the homoplasmy and major alleles of the heteroplasmy. In some embodiments, the primary mtDNA haplogroups are assigned based on the constructed mtDNA sequences using HaploGrep2 (Weissensteiner et al., Nuc. Acids Res., 2016, 44, W58-W63). HaploGrep2 is an algorithm whereby the haplogroup is classified based on precalculated phylogenetic weights that correspond to the mutation occurrence per position in Phylotree. Similar tools for assigning primary mtDNA haplogroups include mthap (world wide web at "dna.jameslick.com/mthap/") and haplofind (world wide web at "haplofind.unibo.it/").

A biological sample that has an assigned primary mtDNA haplogroup that is different than the primary mtDNA haplogroup assigned to a majority of the biological samples from the same individual is an unreliable biological sample. In some embodiments, the unreliable biological sample has been mislabeled. In some embodiments, the unreliable biological sample has been swapped with another biological sample. In some embodiments, the one or more mislabeled samples are re-labeled correctly. In some embodiments, the one or more mislabeled samples are discarded.

In some embodiments, the methods further comprise determining a heteroplasmy number for each biological sample. In some embodiments, the heteroplasmy frequency is determined for each mutation identified in the mtDNA sequences for each biological sample. When a biological sample has a high heteroplasmy number, the biological sample is assigned a secondary mtDNA haplogroup. In some embodiments, a threshold for having a high heteroplasmy number is >10 heteroplasmies.

In some embodiments, assigning the secondary mtDNA haplogroup comprises constructing a secondary mtDNA sequence using the homoplasmy and minor alleles of the heteroplasmy. A biological sample having an assigned secondary mtDNA haplogroup that is different than the assigned primary mtDNA haplogroup is an unreliable sample that is contaminated. The choices for the primary haplogroup are identical to the choices for the secondary haplogroup.

In some embodiments, the methods further comprise determining the level of contamination of a biological sample. In some embodiments the level of contamination is indicated by determining the median of the heteroplasmy frequencies of all heteroplasmies in the contaminated sample. The greater the median heteroplasmy frequency, the greater the level of contamination. There is strong correlation between the real contamination percent and heteroplasmy frequency median/mean. For example, if the median heteroplasmy frequency is 6%, the contamination level is also about 6%.

In some embodiments, the methods further comprise processing the mtDNA sequencing reads obtained from the nucleic acid sequencing assay for quality control and adaptor sequence removal prior to identifying a heteroplasmy and a homoplasmy. In such embodiments, the mtDNA sequencing reads obtained from the nucleic acid sequencing assay are mtDNA raw sequencing reads. In carrying out the processing of the mtDNA raw sequencing reads, quality controlled mtDNA sequencing reads are produced. In some embodiments, the processing of the mtDNA sequencing reads obtained from the nucleic acid sequencing assay for quality control and adaptor sequence removal can be carried out by using "Trimmomatic" (Bolger et al., Bioinformatics, 2014, 30, 2114-2120). This processing step improves the accuracy of the subsequent mtDNA variant identification. Another tool that can be used for processing is cutadpt (world wide web at "cutadapt.readthedocs.io/en/stable/").

In some embodiments, the method further comprises a two-step mapping process prior to identifying a heteroplasmy and a homoplasmy. In some embodiments, the mtDNA sequencing reads obtained from the nucleic acid sequencing assay can be used in the two-step mapping process. In some embodiments, the quality controlled mtDNA sequencing reads obtained from the quality control and adaptor sequence removal process can be used in the two-step mapping process. In these embodiments, the mtDNA sequencing reads (obtained from the nucleic acid sequencing assay) or the quality controlled mtDNA sequencing reads (obtained from the quality control and adaptor sequence removal process) are mapped to a mitochondrial reference genome to produce candidate mtDNA sequencing reads. In some embodiments, the mitochondrial reference genome is the revised Cambridge Reference Sequence (rCRS) for the mitochondrial genome. In some embodiments, the mapping step can be carried out using "bowtie2" (Langmead et al., Nature Methods, 2012, 9, 357-359) or bwa. The candidate mtDNA sequencing reads obtained from the first mapping step are re-mapped to an entire human reference genome. In some embodiments, the human reference genome is GRCh38 for the nuclear genome. In addition, GRCh37 can also be used. In some embodiments, the mapping step can be carried out using "bowtie2".

Upon carrying out the two-step mapping process, the candidate mtDNA sequencing reads are retained under two circumstances: 1) the candidate mtDNA sequencing reads are retained when the candidate mtDNA sequencing read is uniquely mapped to the mitochondrial reference genome, or has fewer mismatches to the mitochondrial reference genome than to the human reference genome; and 2) the candidate mtDNA sequencing reads are retained when the alignment mismatch count of the candidate mtDNA sequencing read is less than 5 mismatched bases.

In some embodiments, the methods further comprise processing the mtDNA sequencing reads (obtained from the nucleic acid sequencing assay) for sorting and duplicate removal. In some embodiments, the methods further comprise processing the quality controlled mtDNA sequencing reads (obtained from the quality control and adaptor sequence removal process) for sorting and duplicate removal. In some embodiments, the methods further comprise performing post-mapping processing of the retained candidate mtDNA sequencing read for sorting and duplicate removal. In some embodiments, the processing for sorting and duplicate removal can be carried out by using the "samtools toolkit" (Li et al., Bioinformatics, 2009, 25, 2078-2079). These processing steps are standard Next Generation Sequencing (NGS) data processing steps. The GATK toolkit can also be used.

In some embodiments, the methods further comprise down-sampling the mtDNA sequencing reads obtained from the nucleic acid sequencing assay to a desired depth prior to identifying the heteroplasmy and the homoplasmy. In some embodiments, the methods further comprise down-sampling the mtDNA sequencing reads obtained from the nucleic acid sequencing assay to a desired depth prior to processing the mtDNA raw sequencing reads for quality control and adaptor sequence removal. In some embodiments, the mtDNA raw sequencing reads from a whole transcriptome data set can be down-sampled to 10 million reads. In some embodiments, the down-sampling can be carried out by using "seqtk" (world wide web at "github.com/lh3/seqtk"). RNA seq data usually has very high mtDNA content. Thus, not all of the sequences are required to perform the methodology described herein because the greater the mtDNA coverage, the longer the computational time will be. In some embodiments, the desired depth is about 1000, but can be as low as about 200. Additional tools that can be used include, for example, FASTQ-SAMPLE (world wide web at "homes.cs.washington.edu/~dcjones/fastq-tools/fastq-sample.html").

In some embodiments, the methods described herein further comprise obtaining the plurality of biological samples from the individual prior to performing the nucleic acid sequencing assay on the plurality of samples. In some embodiments, the biological samples are blood, tissue, or tumor biopsy. In some embodiments, the methods described herein further comprise amplifying nucleic acid molecules in the biological samples prior to performing the nucleic acid sequencing assay on the plurality of samples.

The present disclosure also provides methods of identifying an unreliable biological sample, the methods comprising: a) performing a nucleic acid sequencing assay on each biological sample of a plurality of biological samples obtained from a single individual to obtain DNA raw sequencing reads for each biological sample; b) processing the DNA raw sequencing reads for quality control and adaptor sequence removal to produce quality controlled DNA sequencing reads; c) mapping the quality controlled DNA sequencing reads to a mitochondrial reference genome to produce candidate mtDNA sequencing reads; d) re-mapping the candidate mtDNA sequencing reads to a human reference genome and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5; e) performing post-mapping processing of the retained candidate mtDNA sequencing reads for sorting and duplicate removal; f) identifying heteroplasmy and homoplasmy in the retained candidate mtDNA sequencing reads for each of the biological samples; and g) assigning a primary mtDNA haplogroup to each biological sample, wherein any biological sample having an assigned primary mtDNA haplogroup that is different than the primary mtDNA haplogroup assigned to a majority of the biological samples from the same individual is an unreliable biological sample that is a mislabeled biological sample. The steps of this method can be carried out by the processes described herein.

The present disclosure also provides methods of identifying an unreliable biological sample, the methods comprising: a) performing a nucleic acid sequencing assay on each biological sample of a plurality of biological samples obtained from a single individual to obtain DNA raw sequencing reads for each biological sample; b) processing the DNA raw sequencing reads for quality control and adaptor sequence removal to produce quality controlled DNA sequencing reads; c) mapping the quality controlled DNA sequencing reads to a mitochondrial reference genome to produce candidate mtDNA sequencing reads; d) re-mapping the candidate mtDNA sequencing reads to a human reference genome and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5; e) performing post-mapping processing of the retained candidate mtDNA sequencing reads for sorting and duplicate removal; f) identifying heteroplasmy and homoplasmy in the retained candidate mtDNA sequencing reads for each of the biological samples; g) assigning a primary mtDNA haplogroup to each biological sample; and h) determining the total heteroplasmy number for each biological sample, wherein when a biological sample has a high heteroplasmy number, the biological sample is assigned a secondary mtDNA haplogroup, wherein a biological sample having an assigned secondary mtDNA haplogroup that is different than the assigned primary mtDNA haplogroup is an unreliable sample that is contaminated. The steps of this method can be carried out by the processes described herein.

In some embodiments, the methods described herein can be carried out as a workflow. Numerous workflow management tools such as, for example, Pyflow (see, world wide web at "github.com/Illumina/pyflow"), can be used to streamline the steps together.

The methods described herein have several advantages. First, the methods do not require any nuclear DNA (nDNA) variant information for each sample or at population allele frequency level—this kind of information is often not available for many studies, especially for RNA-seq studies. Second, the methods do not require intensively preprocessed sequencing data as input, such as whole genome mapped bam files, whole genome variants VCF files. The methods can directly take fastq files as input. Third, the methods can be applied to low-coverage sequencing data. nDNA variants-based methods usually need high coverage (>50×) to detect low-level contaminations. Due to multiple-copy nature of mtDNA, even for the low coverage data, for example, 2 to 4× for 1000 Genomes Project, mtDNA coverage still can be as high as 1000 to 2000×, which is sufficient to detect contamination level as low as 1%. Fourth, the methods do not require high computational power, a typical sample with 1000× mtDNA coverage can be processed in 10 to 20 minutes with a single processor and 4Gb memory. Samples with high mtDNA contents can take longer to process but can be down-sampled to shorten the processing time. The methods can be easily incorporated into standard NGS data processing pipelines and serve as an important quality control step by identifying problematic samples and further improving the accuracy of downstream data analysis.

The following representative embodiments are presented:

Embodiment 1. A method of identifying an unreliable biological sample, the method comprising: performing a nucleic acid sequencing assay on each biological sample of a plurality of biological samples obtained from a single individual to obtain mitochondrial DNA (mtDNA) sequencing reads for each biological sample; identifying a heteroplasmy and a homoplasmy in the mtDNA sequencing reads from the previous step for each of the biological samples; and assigning a primary mtDNA haplogroup to each biological sample, wherein any biological sample having an assigned primary mtDNA haplogroup that is different than the primary mtDNA haplogroup assigned to a majority of the biological samples from the same individual is an unreliable biological sample that is a mislabeled biological sample.

Embodiment 2. The method according to embodiment 1, wherein the heteroplasmy is identified by determining the sequencing coverage, a minor allele frequency, and presence of the minor allele, wherein a heteroplasmy is present when: i) the sequencing coverage is 50; ii) the minor allele frequency is 1%; and iii) for DNA data, the minor allele is observed at least twice from each strand, or for RNA data, the minor allele is observed at least three times.

Embodiment 3. The method according to embodiment 1 or embodiment 2, wherein the homoplasmy is identified by determining the sequencing coverage and the presence of one or more alleles, wherein a homoplasmy is present when: i) the sequencing coverage is >10; and ii) only one allele is observed at a particular nucleic acid site and it is different than the corresponding reference allele, or multiple alleles are observed at a particular nucleic acid site and the major allele is different than the corresponding reference allele, and the particular nucleic acid site fails heteroplasmy criteria.

Embodiment 4. The method according to any one of embodiments 1 to 3, wherein assigning the primary mtDNA haplogroup to each biological sample comprises constructing a mtDNA sequence for each biological sample using the homoplasmy and major alleles of the heteroplasmy.

Embodiment 5. The method according to any one of embodiments 1 to 4, the method further comprising determining the total heteroplasmy number for each biological sample, wherein when a biological sample has a high heteroplasmy number, the biological sample is assigned a secondary mtDNA haplogroup.

Embodiment 6. The method according to embodiment 5, wherein assigning the secondary mtDNA haplogroup comprises constructing a secondary mtDNA sequence using the homoplasmy and minor alleles of the heteroplasmy, wherein a biological sample having an assigned secondary mtDNA haplogroup that is different than the assigned primary mtDNA haplogroup is an unreliable biological sample that is contaminated.

Embodiment 7. The method according to embodiment 6, the method further comprising determining the level of contamination of a biological sample by determining the median of the heteroplasmy frequencies of all heteroplasmies in the contaminated biological sample, wherein the greater the median of the heteroplasmy frequency, the greater the level of contamination.

Embodiment 8. The method according to any one of embodiments 1 to 7, the method further comprising, prior to identifying a heteroplasmy and a homoplasmy, processing the mtDNA sequencing reads obtained from the nucleic acid sequencing assay for quality control and adaptor sequence removal to produce quality controlled mtDNA sequencing reads.

Embodiment 9. The method according to embodiment 8, the method further comprising: mapping the quality controlled mtDNA sequencing reads to a mitochondrial reference genome to produce candidate mtDNA sequencing reads; and re-mapping the candidate mtDNA sequencing reads to a human reference genome, and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5.

Embodiment 10. The method according to embodiment 9, the method further comprising performing post-mapping processing of the retained candidate mtDNA sequencing read for sorting and duplicate removal.

Embodiment 11. The method according to any one of embodiments 1 to 10, the method further comprising down-sampling the mtDNA sequencing reads obtained from the nucleic acid sequencing assay to a desired depth prior to identifying the heteroplasmy and the homoplasmy and/or prior to processing the mtDNA sequencing reads for quality control and adaptor sequence removal.

Embodiment 12. The method according to any one of embodiments 1 to 11, the method further comprising obtaining the plurality of biological samples from the individual prior to performing the nucleic acid sequencing assay on the plurality of biological samples.

Embodiment 13. The method according to any one of embodiments 1 to 12, wherein the biological samples are blood or tissue.

Embodiment 14. The method according to any one of embodiments 1 to 13, the method further comprising amplifying nucleic acid molecules in the biological samples prior to performing the nucleic acid sequencing assay on the plurality of biological samples.

Embodiment 15. The method according to any one of embodiments 1 to 14, the method further comprising correctly labeling the one or more mislabeled biological samples or discarding the one or more mislabeled biological samples.

Embodiment 16. The method according to any one of embodiments 1 to 14, the method further comprising discarding the one or more contaminated biological samples.

Embodiment 17. The method according to any one of embodiments 1 to 16, wherein the sequencing assay comprises next generation sequencing (NGS).

Embodiment 18. The method according to embodiment 17, wherein the NGS comprises whole genome sequencing.

Embodiment 19. The method according to embodiment 17, wherein the NGS comprises whole exome sequencing.

Embodiment 20. The method according to embodiment 17, wherein the NGS comprises RNA sequencing.

Embodiment 21. The method according to embodiment 17, wherein the NGS comprises bisulfite sequencing.

Embodiment 22. A method of identifying an unreliable biological sample, the method comprising: performing a nucleic acid sequencing assay on each biological sample of a plurality of biological samples obtained from a single individual to obtain mitochondrial DNA (mtDNA) raw sequencing reads for each biological sample; processing the mtDNA raw sequencing reads for quality control and adaptor sequence removal to produce quality controlled mtDNA sequencing reads; mapping the quality controlled mtDNA sequencing reads to a mitochondrial reference genome to produce candidate mtDNA sequencing reads; re-mapping the candidate mtDNA sequencing reads to a human reference genome and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5; performing post-mapping processing of the retained candidate mtDNA sequencing reads for sorting and duplicate removal; identifying heteroplasmy and homoplasmy in the retained candidate mtDNA sequencing reads for each of the biological samples; and assigning a primary mtDNA haplogroup to each biological sample, wherein any biological sample having an assigned primary mtDNA haplogroup that is different than the primary mtDNA haplogroup assigned to a majority of the biological samples from the same individual is an unreliable biological sample that is a mislabeled biological sample.

Embodiment 23. A method of identifying an unreliable biological sample, the method comprising: performing a nucleic acid sequencing assay on each biological sample of a plurality of biological samples obtained from a single individual to obtain mitochondrial DNA (mtDNA) raw sequencing reads for each biological sample; processing the mtDNA raw sequencing reads for quality control and adaptor sequence removal to produce quality controlled mtDNA sequencing reads; mapping the quality controlled mtDNA sequencing reads to a mitochondrial reference genome to produce candidate mtDNA sequencing reads; re-mapping the candidate mtDNA sequencing reads to a human reference genome and retaining the candidate mtDNA sequencing reads when: i) the candidate mtDNA sequencing read is uniquely mapped to the mitochondrial reference genome or has fewer mismatches to the mitochondrial reference genome than to the human reference genome; and ii) the alignment mismatch count of the candidate mtDNA sequencing read is less than 5; performing post-mapping processing of the retained candidate mtDNA sequencing reads for sorting and duplicate removal; identifying heteroplasmy and homoplasmy in the retained candidate mtDNA sequencing reads for each of the biological samples; assigning a primary mtDNA haplogroup to each biological sample; and determining the total heteroplasmy number for each biological sample, wherein when a biological sample has a high heteroplasmy number, the biological sample is assigned a secondary mtDNA haplogroup, wherein a biological sample having an assigned secondary mtDNA haplogroup that is different than the assigned primary mtDNA haplogroup is an unreliable sample that is contaminated.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: mtDNA Variation Identification and Haplogroup Assignment

General Methodology mtDNA variations (both homoplasmy and heteroplasmy) are identified from next generation sequencing data by, for example, performing an analysis represented in FIG. 1 (see, Box 1). Upon performing a nucleic acid sequencing assay on a plurality of biological samples, raw sequencing reads can be down-sampled to a desired depth to lower the computational burden (see, FIG. 1, Box 1, "Step0") using "seqtk" that can be found at, for example, the world wide web at "github.com/lh3/seqtk". This step is optional and need not be performed.

The raw mtDNA sequencing reads obtained from the nucleic acid sequencing assay, optionally from the previous down-sampling step, are processed for quality control and adaptor sequence removal by using "Trimmomatic" (Bolger et al., Bioinformatics, 2014, 30, 2114-2120) (see, FIG. 1, Box 1, "Step1").

To retrieve candidate mtDNA sequencing reads, the quality controlled sequencing reads are mapped to the mitochondrial reference genome (revised Cambridge Reference Sequence, rCRS) with "bowtie2" (Langmead et al., Nature Methods, 2012, 9, 357-359) (see, FIG. 1, Box 1, "Step2"). Nuclear mitochondrial DNA segments (NUMTs) in nuclear genome may be mismapped to the mitochondrial genome and counted as mtDNA reads. To minimize the effect of NUMTs, a second-round mapping can be performed whereby the mapped reads from first round are re-mapped to the entire human reference genome, GRCh38 for the nuclear genome and the revised Cambridge Reference Sequence (rCRS) for the mitochondrial genome. Reads (or read pairs) are retained if: a) reads (read pairs) are uniquely mapped to the mitochondrial genome or have less mismatches to the mitochondrial genome than to the nuclear genome; and b) the alignment mismatch count is less than 5.

The retained candidate mtDNA sequencing reads are further processed by "samtools toolkit" (Li et al., Bioinformatics, 2009, 25, 2078-2079), including sam to bam conversion, sorting and duplication removal (see, FIG. 1, Box 1, "Step3").

The retained candidate mtDNA sequencing reads for each mtDNA site are compiled with "samtools mpileup function" (Li et al., Bioinformatics, 2009, 25, 2078-2079), and bases are further filtered by sequencing quality ($>=20$), and heteroplasmies and homoplasmies are identified (see, FIG. 1, Box 1, "Step4"). Heteroplasmies are identified with the following criteria: a) sequencing coverage $>=50$; b) minor allele frequency $>=1\%$; and c) for DNA data, a minor allele must be observed at least twice from each strand, and for RNA data, a minor allele must be observed at least three times. Homoplasmies are identified with following criteria: a) sequencing coverage $>10$; and b1) only one allele is observed at the given site and it is different from the reference allele, or b2) multiple alleles are observed and the major allele is different from the reference, but the site fails heteroplasmy criteria.

mtDNA sequences for each sample are constructed with the homoplasmy information and the major alleles at heteroplasmy sites, and haplogroups are assigned based on the constructed sequences using "HaploGrep2" (Weissensteiner et al., Nuc. Acids Res., 2016, 44, W58-W63) (see, FIG. 1, Box 1, "Step5"). The assigned haplogroup at this step is referred to as the primary haplogroup for each sample.

If a particular sample has an unusual high heteroplasmy number, a secondary mtDNA sequence is constructed with the homoplasmy information and the minor alleles at the heteroplasmy sites, and a secondary haplogroup will be assigned based on this secondary mtDNA sequence. (see, FIG. 1, Box 1, "Step6").

Sample Mislabeling/Swap Detection (See, FIG. 1, Box 2)

In a plurality of samples, each sample can be assigned a primary haplogroup as described herein. In the case where all samples are processed accurately, all samples from the same individual will be assigned to the same haplogroup. On the contrary, if two or more haplogroups were assigned among these samples, the sample(s) with a minority haplogroup assignment are considered haplogroup unmatched (i.e., mislabeled or swapped with another sample). For example, in Table 1 below, sample 001 is considered to be swapped with sample 008.

TABLE 1

| sample ID | subject ID | haplogroup | unmatched |
|---|---|---|---|
| 001 | A | J2b1a1 | yes |
| 002 | A | H1ba | no |
| 003 | A | H1ba | no |
| 004 | A | H1ba | no |
| 005 | B | J2b1a1 | no |
| 006 | B | J2b1a1 | no |
| 007 | B | J2b1a1 | no |
| 008 | B | H1ba | yes |

Sample Contamination Detection and Quantification (See, FIG. 1, Box 3)

If an unusual high heteroplasmy number is observed in a particular sample, the sample is potentially contaminated. The primary and secondary haplogroups are assigned to the suspected sample based on the major alleles and minor alleles on the heteroplasmy sites, respectively (see, FIG. 1, Box 1, "Step5" and "Step6"). If the primary and secondary haplogroups are different, the sample is considered to be a contaminated sample. When a sample is determined to be contaminated, the median of the frequencies of all the heteroplasmies in the sample is used to represent the contamination level.

Example 2: Use of mtDNA Haplogroup to Detect a Mislabeled Sample

Samples are collected from several individuals and each individual has multiple samples. After obtaining RNA-seq data for a batch of clinical samples, mtDNA haplogroups are assigned to each sample (see, Table 2). Samples collected from the same individual should belong to the same mtDNA haplogroup. Unmatched mtDNA haplogroups suggests possible sample mislabeling. The sample with the haplogroup L3h1a1 should be considered a mislabeled sample.

TABLE 2

| Sample ID | Subject ID | Haplogroup |
|---|---|---|
| 001 | A | T2 + 16189 |
| 02 | A | T2 + 16189 |
| 003 | A | T2 + 16189 |
| 004 | A | L3h1a1 |
| 005 | A | T2 + 16189 |

Example 3: Use of mtDNA Heteroplasmy to Detect Sample Contamination

Virtual Contamination Sample Preparation

Whole genome sequencing fastq files of two individuals, HG00290 and NA19086, were downloaded from 1000 Genome Project (see, ftp site at "ftp.1000genomes.ebi.ac.uk/vol1/ftp/"). Sequencing reads were sampled from the two individuals, and NA19086 reads were mixed into HG00290 at different ratios (0.1%, 0.5%, 1%, 2%, 5%, 10%, 20%, 30%, and 40%) to create virtual contamination samples.
Real-World Datasets DNA sequencing data were downloaded from 1000 Genome Project (see, ftp site at "ftp.1000genomes.ebi.ac.uk/vol1/ftp/"). For each individual, reads mapped to mitochondrial genome were extracted by samtools (Li et al., Bioinformatics, 2009, 25, 2078-2079) from the bam file and subsequently converted to pair end fastq files. The fastq files were used as the input for the methods described herein.

Fastq files of two RNA-seq studies were downloaded from GEO at GSE81266 and GSE127165. GSE81266 contained whole transcriptome data for 77 ileum and prepouch ileum samples, including 61 pair end (2×75 bp) and 16 single end (50 bp) samples. GSE127165 contained whole transcriptome data from 57 laryngeal squamous cell carcinoma patients, each patient had a tumor sample and an adjacent normal sample. All samples were pair end with 150 bp read length.
Analytical Performance Virtual contamination samples were analyzed. Whole genome sequencing data of two individuals, HG00290 and NA19086, were downloaded from 1000 Genomes Project (Auton et al., Nature, 2015, 526, 68-74). HG00290 belonged to haplogroup U5a2a1a and one heteroplasmy was identified in this individual's mtDNA genome (2610T>C 1.4%), while NA19086 belonged to haplogroup D4b1a1 and two heteroplasmies were identified (1646T>C 2.1%, 12785T>T 21.3%). The two individuals had 45 nucleotide differences in their mitochondrial genome.

Virtual contamination samples were created by mixing the sequencing reads from the two samples at a series ratio, ranging from 0.1% to 40%. HG00290 was treated as the original sample and NA19086 was treated as the contaminant. Each contamination sample contained 50 million read pairs with read length 100 bp. The virtual contaminated samples were processed by the methods described herein for contamination analysis and the results are summarized in FIG. 3. When the contamination levels were above 2%, 45-46 heteroplasmies were identified from the samples, much higher than the normal range (1 to 2 heteroplasmies in an individual). These heteroplasmies covered almost all the expected sites (the 45 segregating sites between the two individuals plus the original heteroplasmy 2610 T>C in HG00290). Only one expected site was missed in the 2% sample. The primary haplogroups were U5a2a1a for all 6 samples, which was same as the original sample HG00290 and the secondary haplogroup was D4b1a1, same as the contaminant. When the contamination level was 1%, 29 heteroplasmies were detected. The 17 missing sites were manually checked and it was determined that these sites all showed some heteroplasmy signal, but because the heteroplasmy frequency identification cutoff was set at 1%, those sites did not make the cutoff. The secondary haplogroup of the 1% sample was correctly assigned to D4b1a1. Only 1 and 11 heteroplasmies were detected when the contamination levels were 0.1% and 0.5%, and the secondary haplogroups for these two samples were still U5a2a1a, therefore, contamination cannot be confidently detected in these low contamination level samples. These results indicate that by combining the heteroplasmy number and secondary haplogroup assignment, contaminations as low as 1% were able to be detected.

Figure 2A:
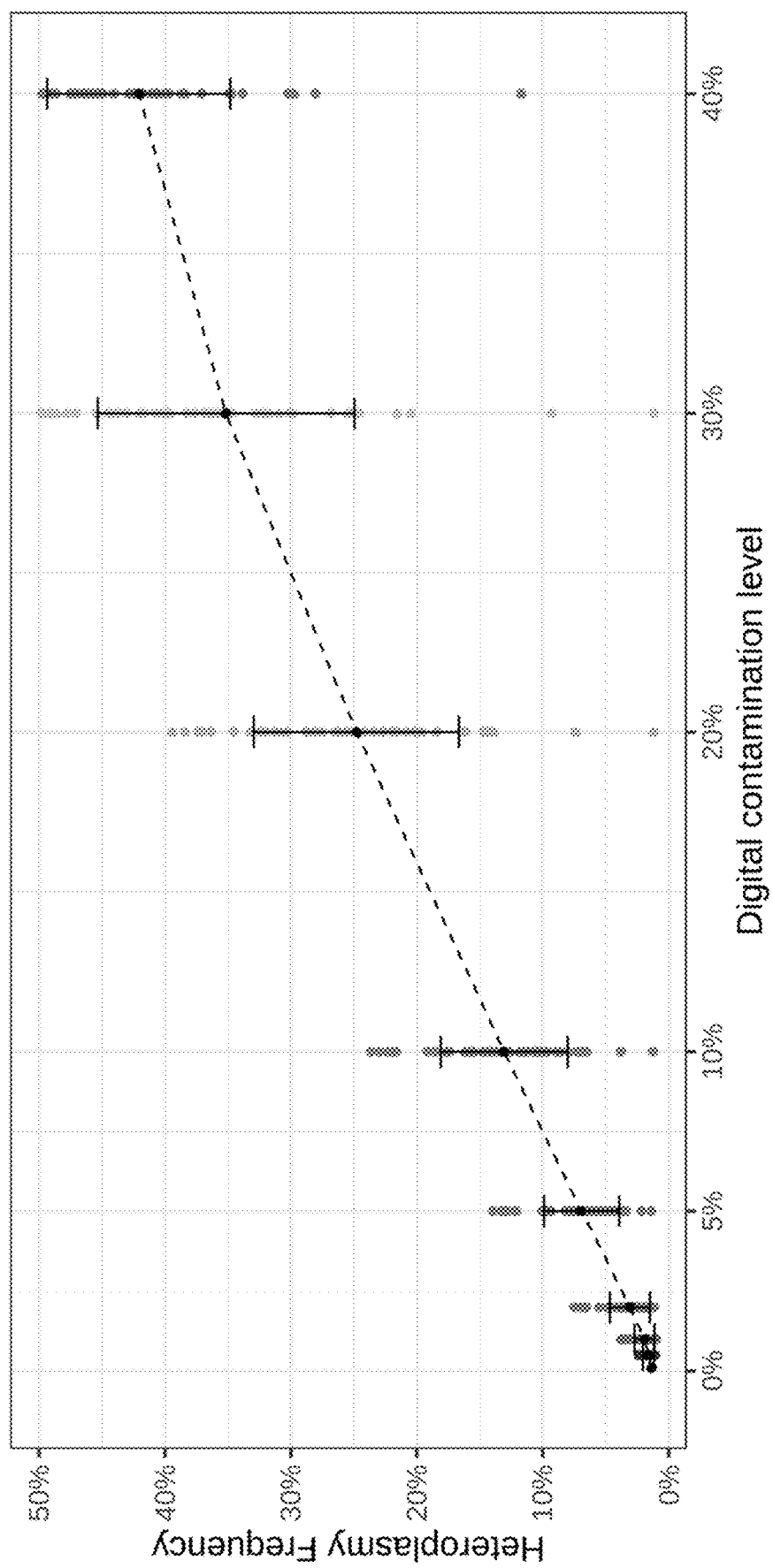
FIG. 2A shows the performance of the methods described herein on virtual contamination samples. Virtual contamination samples were created by mixing two samples from 1000 Genomes Project at different ratios. The X-axis indicates the theoretical contamination level and the Y-axis indicates the heteroplasmy frequencies identified from each virtual contamination sample. Each colored dot represents one heteroplasmy, the black dots represent the means of the heteroplasmy frequencies in the samples and error bars represent the frequency standard errors. The mean of the frequencies is significantly correlated with theoretical contamination level (Pearson correlation=0.996781, P value=6.212e-09).
Figure 2B:
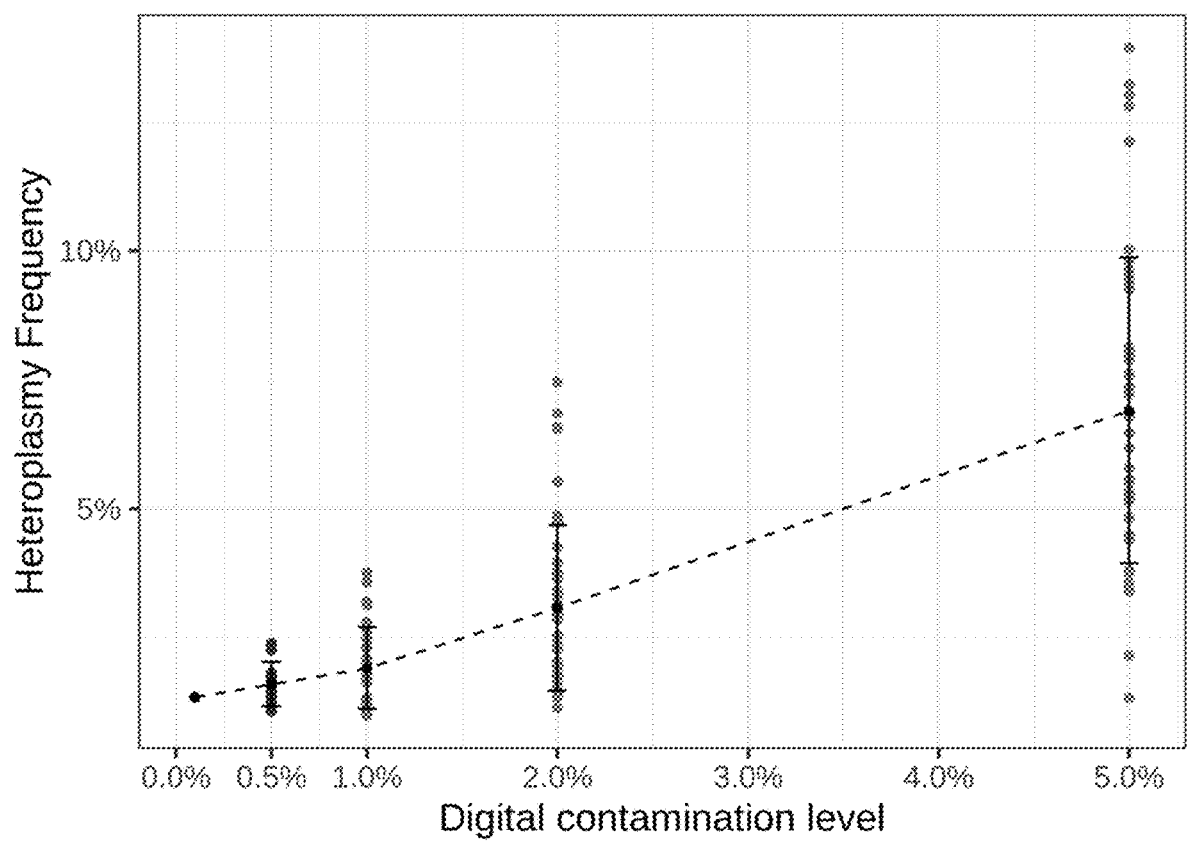
FIG. 2B shows the performance of the methods described herein on virtual contamination samples. Virtual contamination samples were created by mixing two samples from 1000 Genomes Project at different ratios. The X-axis indicates the theoretical contamination level and the Y-axis indicates the heteroplasmy frequencies identified from each virtual contamination sample. Each colored dot represents one heteroplasmy, the black dots represent the means of the heteroplasmy frequencies in the samples and error bars represent the frequency standard errors. The mean of the frequencies is significantly correlated with theoretical contamination level (Pearson correlation=0.996781, P value=6.212e-09).

The heteroplasmy frequencies in the artificial contamination samples were further evaluated. There were some fluctuations of the heteroplasmy frequencies in each sample, but the mean and median of the frequencies were significantly correlated with theoretical contamination level (see, FIGS. 2A-2B, and FIG. 3; Pearson correlation=0.996781, 0.9979935, P value=6.212e-09, 1.189e-09 for mean and median, respectively). Therefore, when a given sample is detected as contaminated by the methods described herein, the contamination level can be relatively quantified by the mean/median of the heteroplasmy frequencies in the sample.

Real-World Data Application: RNA-seq Data

There are several factors that can make the low-frequency (<5%) heteroplasmies identification more challenging in RNA-seq data than that in DNA-seq data: 1) errors introduced during reverse transcription step; 2) RNA editing/modification; and/or 3) uneven coverage across the mtDNA genome due to varied gene expression levels. Therefore, to reduce the false positive heteroplasmies, only heteroplasmies with frequency >5% was considered as reliable heteroplasmies in RNA data. In addition, three well defined mtDNA editing sites: 295, 2617 and 13710 (Bar-Yaacov et al., Genome Res., 2013, 23, 1789-1796; and Hodgkinson et al., Science, 2014, 344, 413-415) were excluded.

The methods described herein were applied to two bulk RNA-seq datasets to evaluate different disease or tissue type context. First, the methods described herein were applied to a dataset with 77 samples from 25 subjects (Huang et al., Inflamm. Bowel Dis., 2017, 23, 366-378). Most subjects in this study had samples from different tissues (ileum and prepouch ileum) and/or at different biopsy time points (4 months, 8 months, 12 months etc.). 16 samples in this dataset were single end samples with 50 bp read length and 61 were pair end samples with 75 read length. For each sample, 10 million reads (pairs) were randomly sampled to test. The primary haplogroup assignments to the samples were first evaluated. In this dataset, samples from the same subject were all assigned to the same mtDNA haplogroup (see, FIG. 4A-4G), indicating that there was no sample swapping. Potential contaminations in those samples was evaluated next. At 5% heteroplasmy frequency cutoff, except sample SRR3493833, all other samples had at most 6 heteroplasmies and the secondary haplogroup assignments were the same as the primary haplogroup (see, FIG. 4A-4G). In sample SRR3493833, 29 heteroplasmies were identified, much higher than the normal range, and the median frequency of the heteroplasmies was 14.8%. The secondary haplogroup of this sample was J1c8a, which was also different from the primary haplogroup U5b2a1a. These results indicated that sample SRR3493833 was potentially contaminated by another sample from J1 haplogroup and the contamination level was about 14.8%.

The methods described herein were also applied to a dataset involving tumor samples (Wu et al., Molec. Cancer, 2020, 19, 99). This dataset contained samples from 57 laryngeal squamous cell carcinoma patients, each has a tumor sample and a paired adjacent normal mucosa sample. In this dataset, the paired tumor sample and adjacent normal sample from the same patient were all assigned to the same haplogroup (see, FIG. 5A-5H), no sample swap was detected. All samples have low heteroplasmy numbers and same primary and secondary haplogroup assignment—therefore, there was also no detectable contamination. By this dataset, the methods described herein were demonstrated to be able to identify tumor sample identities.

Early and accurate sample swapping and contamination detection is a critical quality control step for large scale NGS data, since it can filter out suspected samples and improve the quality for subsequent analysis. In these examples, an efficient method is presented to detect sample swapping and cross-individual contamination by using mtDNA variations identified from the NGS data. The methodology can take demultiplexed fastq files as input without any data preprocessing. It will first detect any sample swapping for individual with multiple samples. It will further detect and quantify potential contamination then suggest the source sample of the contaminants. Although whole genome DNA sequencing data from 1000 Genomes Project and two bulk RNA-seq datasets were used as working examples for these examples, the methods described herein can be generalized to any NGS dataset containing mtDNA reads, such as whole exome sequencing data with offsites mtDNA reads, single cell RNA-seq, ATAC-seq data, etc. The simulation results described herein show that the methods described herein effectively detected contamination as low as 1%.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of identifying one or more contaminated biological samples, the method comprising:
    performing a nucleic acid sequencing assay on each biological sample of a plurality of biological samples obtained from a single individual to obtain mitochondrial DNA (mtDNA) sequencing reads for each biological sample;
    identifying a heteroplasmy and a homoplasmy in the mtDNA sequencing reads from the previous step for each of the biological samples;
    assigning a primary mtDNA haplogroup to each biological sample;
    determining the total heteroplasmy number for each biological sample;
    assigning a biological sample having a high heteroplasmy number to a secondary mtDNA haplogroup;
    detecting biological sample having an assigned secondary mtDNA haplogroup that is different than the primary mtDNA haplogroup assigned to a majority of the biological samples from the same individual;
    determining that the biological sample having an assigned secondary mtDNA haplogroup that is different than the primary mtDNA haplogroup assigned to a majority of the biological samples from the same individual is a contaminated biological sample; and
    discarding the one or more contaminated biological samples.

2. The method according to claim 1, wherein identifying the heteroplasmy comprises determining the sequencing coverage, a minor allele frequency, and presence of the minor allele, wherein a heteroplasmy is present when:
    i) the sequencing coverage is ≥50;
    ii) the minor allele frequency is ≥1%; and
    iii) for DNA data, the minor allele is observed at least twice from each strand, or for RNA data, the minor allele is observed at least three times.

3. The method according to claim 1, wherein identifying the homoplasmy comprises determining the sequencing coverage and the presence of one or more alleles, wherein a homoplasmy is present when:
    i) the sequencing coverage is ≥10; and
    ii) only one allele is observed at a particular nucleic acid site and it is different than the corresponding reference allele, or multiple alleles are observed at a particular nucleic acid site and the major allele is different than the corresponding reference allele, and the particular nucleic acid site fails heteroplasmy criteria.

4. The method according to claim 1, wherein assigning the primary mtDNA haplogroup to each biological sample comprises constructing a mtDNA sequence for each biological sample using the homoplasmy and major alleles of the heteroplasmy.

5. The method according to claim 1, wherein assigning the secondary mtDNA haplogroup comprises constructing a secondary mtDNA sequence using the homoplasmy and minor alleles of the heteroplasmy, and identifying a biological sample having an assigned secondary mtDNA haplogroup that is different than the assigned primary mtDNA haplogroup as an unreliable biological sample that is contaminated.

6. The method according to claim 5, the method further comprising determining the level of contamination of a biological sample by determining the median of the heteroplasmy frequencies of all heteroplasmies in the contaminated biological sample, wherein the greater the median of the heteroplasmy frequency, the greater the level of contamination.

7. The method according to claim 1, the method further comprising, prior to identifying a heteroplasmy and a homoplasmy, processing the mtDNA sequencing reads obtained from the nucleic acid sequencing assay for quality control and adaptor sequence removal to produce quality controlled mtDNA sequencing reads.

8. The method according to claim 7, the method further comprising:
mapping the quality controlled mtDNA sequencing reads to a mitochondrial reference genome to produce candidate mtDNA sequencing reads; and
mapping the candidate mtDNA sequencing reads to a human reference genome, and
retaining the candidate mtDNA sequencing reads when:
  i) the candidate mtDNA sequencing read is uniquely mapped to the mitochondrial reference genome or has fewer mismatches to the mitochondrial reference genome than to the human reference genome; and
  ii) the alignment mismatch count of the candidate mtDNA sequencing read is less than 5.

9. The method according to claim 8, the method further comprising performing post-mapping processing of the retained candidate mtDNA sequencing read for sorting and duplicate removal.

10. The method according to claim 1, the method further comprising down-sampling the mtDNA sequencing reads obtained from the nucleic acid sequencing assay to a desired depth prior to identifying the heteroplasmy and the homoplasmy and/or prior to processing the mtDNA sequencing reads for quality control and adaptor sequence removal.

11. The method according to claim 1, the method further comprising obtaining the plurality of biological samples from the individual prior to performing the nucleic acid sequencing assay on the plurality of biological samples.

12. The method according to claim 1, wherein the biological samples are blood or tissue.

13. The method according to claim 1, the method further comprising amplifying nucleic acid molecules in the biological samples prior to performing the nucleic acid sequencing assay on the plurality of biological samples.

14. The method according to claim 1, wherein the sequencing assay comprises next generation sequencing (NGS).

15. The method according to claim 14, wherein the NGS comprises whole genome sequencing.

16. The method according to claim 14, wherein the NGS comprises whole exome sequencing.

17. The method according to claim 14, wherein the NGS comprises RNA sequencing.

18. The method according to claim 14, wherein the NGS comprises bisulfite sequencing.

19. A method of identifying one or more contaminated biological samples, the method comprising:
performing a nucleic acid sequencing assay on each biological sample of a plurality of biological samples obtained from a single individual to obtain mitochondrial DNA (mtDNA) raw sequencing reads for each biological sample;
processing the mtDNA raw sequencing reads for quality control and adaptor sequence removal to produce quality controlled mtDNA sequencing reads;
mapping the quality controlled mtDNA sequencing reads to a mitochondrial reference genome to produce candidate mtDNA sequencing reads;
mapping the candidate mtDNA sequencing reads to a human reference genome and
retaining the candidate mtDNA sequencing reads when:
  i) the candidate mtDNA sequencing read is uniquely mapped to the mitochondrial reference genome or has fewer mismatches to the mitochondrial reference genome than to the human reference genome; and
  ii) the alignment mismatch count of the candidate mtDNA sequencing read is less than 5;
performing post-mapping processing of the retained candidate mtDNA sequencing reads for sorting and duplicate removal;
identifying heteroplasmy and homoplasmy in the retained candidate mtDNA sequencing reads for each of the biological samples;
assigning a primary mtDNA haplogroup to each biological sample;
determining the total heteroplasmy number for each biological sample;
assigning a biological sample having a high heteroplasmy number to a secondary mtDNA haplogroup;
detecting a biological sample having an assigned secondary mtDNA haplogroup that is different than the primary mtDNA haplogroup assigned to a majority of the biological samples from the same individual;
determining that the biological sample having an assigned secondary mtDNA haplogroup that is different than the assigned primary mtDNA haplogroup is a contaminated biological sample; and
discarding the one or more contaminated biological samples.

* * * * *